US00PP28513P2

(12) United States Plant Patent
Koekkoek

(10) Patent No.: US PP28,513 P2
(45) Date of Patent: Oct. 10, 2017

(54) CARNATION PLANT NAMED 'HILBEAGISEL'

(50) Latin Name: ***Dianthus* L.**
Varietal Denomination: Hilbeagisel

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 14/999,646

(22) Filed: Jun. 8, 2016

(51) Int. Cl.
*A01H 5/02* (2006.01)

(52) U.S. Cl.
USPC ..... Plt./279

(58) Field of Classification Search
USPC ..... Plt./279
See application file for complete search history.

*Primary Examiner* — Annette Para
(74) *Attorney, Agent, or Firm* — C. A. Whealy

(57) ABSTRACT

A new and distinct cultivar of Carnation plant named 'Hilbeagisel', characterized by its compact, uniformly mounding and upright to broadly spreading plant habit; relatively small leaves; freely flowering habit; white-colored single flowers; and good container performance.

1 Drawing Sheet

Botanical designation: *Dianthus* L.
Cultivar denomination: 'HILBEAGISEL'.

BACKGROUND OF THE INVENTION

The present invention relates to a new and distinct cultivar of Carnation plant, botanically known as *Dianthus* L., grown commercially as a container plant and hereinafter referred to by the name 'Hilbeagisel'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in June, 2011 of a proprietary selection of *Dianthus* L. identified as code number 1851, not patented, as the female, or seed, parent with a proprietary selection of *Dianthus* L. identified as code number 1814, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal cuttings propagated in a controlled greenhouse environment in De Kwakel, The Netherlands since October, 2012 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbeagisel'. These characteristics in combination distinguish 'Hilbeagisel' as a new and distinct Carnation plant:

1. Compact, uniformly mounding and upright to broadly spreading plant habit.
2. Relatively small leaves.
3. Freely flowering habit.
4. White-colored single flowers.
5. Good container performance.

Plants of the new Carnation differ primarily from plants of the female parent selection in the following characteristics:

1. Plants of the new Carnation are more freely branching than plants of the female parent selection.
2. Plants of the new Carnation have larger flowers than plants of the female parent selection.
3. Plants of the new Carnation and the female parent selection differ in flower color as plants of the female parent selection have light pink-colored flowers.

Plants of the new Carnation differ primarily from plants of the male parent selection in the following characteristics:

1. Plants of the new Carnation have stronger branches than plants of the male parent selection.
2. Plants of the new Carnation flower earlier than plants of the male parent selection.
3. Plants of the new Carnation have larger flowers than plants of the male parent selection.
4. Plants of the new Carnation and the male parent selection differ in flower color as plants of the male parent selection have light pink-colored flowers.

Plants of the new Carnation also can be compared to plants of *Dianthus* L. 'Hilbeadouz', not patented. In side-by-side comparisons, plants of the new Carnation differ primarily from plants of 'Hilbeadouz' in the following characteristics:

1. Plants of the new Carnation have longer branches than plants of 'Hilbeadouz'.
2. Plants of the new Carnation flower earlier than plants of 'Hilbeadouz'.

3. When exposed to low temperatures, plants of the new Carnation and 'Hilbeadouz' differ in flower color as plants of 'Hilbeadouz' have light pink-colored flowers.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilbeagisel' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 17° C., night temperatures averaged 12° C. and light levels averaged 7,000 lux. Plants used for the photograph and description were twelve weeks old. In the following description, color references are made to The Royal Horticultural Society Colour Chart, 2015 Edition, except where general terms of ordinary dictionary significance are used.

Botanical classification: *Dianthus* L. 'Hilbeagisel'.

Parentage:

*Female, or seed, parent*.—Proprietary selection of *Dianthus* L. identified as code number 1851, not patented.

*Male, or pollen, parent*.—Proprietary selection of *Dianthus* L. identified as code number 1814, not patented.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; growth habit, moderate to low vigor.

*Plant height, soil level to top of foliar plane*.—About 11.7 cm.

*Plant height, soil level to top of floral plane*.—About 17.1 cm.

*Plant diameter or spread*.—About 27 cm.

*Lateral branches*.—Branching habit: Freely branching habit with about 24 main (basal) stems; each main stem with about four lateral branches; pinching enhances lateral branch development. Length: About 5,1 cm. Diameter: About 1 mm. Internode length: About 1.6 cm. Strength: Strong. Aspect: Upright to about 45° from vertical. Texture and luster: Smooth, glabrous; moderately glossy. Color, developing: Close to 145B; at internodes, close to 145A. Color, developed: Close to 137C.

Leaf description:

*Arrangement*.—Opposite, simple; sessile.

*Length*.—About 5.8 cm.

*Width*.—About 3 mm.

*Shape*.—Narrowly oblanceolate; moderately carinate.

*Apex*.—Acute.

*Base*.—Attenuate; decurrent.

*Margin*.—Entire.

*Texture and luster, upper and lower surfaces*.—Smooth, glabrous; matte.

*Venation pattern*.—Parallel.

*Color*.—Developing leaves, upper and lower surfaces: Close to 137C; towards the base, fading to close to 143B. Fully expanded leaves, upper surface: Close to 137A; venation, close to 137A. Fully expanded leaves, lower surface: Close to 137B; venation, close to 143A.

Flower description:

*Flower form and flowering habit*.—Single flowers arranged singly or in pairs; freely flowering habit with about 140 flowers developing during the flowering season; flowers face mostly upright to outwardly.

*Natural flowering season*.—Flowering is continuous from the spring to late summer in The Netherlands; plants begin flowering about 9 to 13 weeks after planting.

*Postproduction longevity*.—Flowers last about ten days on the plant; flowers not persistent.

*Fragrance*.—Faintly fragrant; clove-like, sweet.

*Flower buds*.—Length: About 2.3 cm. Diameter: About 4 mm. Shape: Oblanceolate. Texture and luster: Smooth, glabrous; matte. Color: Close to 137C; towards the base, close to 145A; petal apices, close to NN155A.

*Flower diameter*.—About 3.1 cm.

*Flower depth*.—About 2.2 cm.

*Petals*.—Quantity and arrangement: Five petals arranged in a single whorl. Length: About 3 cm. Width: About 1.7 cm. Shape: Spatulate. Apex: Praemorse. Base: Narrowly cuneate, Margin: Distally, dentate; proximally, entire; undulate. Texture and luster, upper surface: Mostly smooth and glabrous, proximally, sparsely pubescent, velvety; slightly glossy. Texture and luster, lower surface: Smooth, glabrous, velvety; slightly glossy. Color: When opening and fully opened, upper surface: Close to NN155B; at the base, close to 145C; color does not change with development; venation, similar to lamina colors. When opening and fully opened, lower surface: Close to 157D; towards the margins and apex, close to NN155B; at the base, close to 145B; color does not change with development; venation, similar to lamina colors. Petaloids: Petaloid development has not been observed on plants of the new Carnation.

*Sepals*.—Quantity and arrangement: Five sepals arranged in a single whorl; proximal 77.5% portion of the sepals are fused into a campanulate-shaped calyx. Calyx length: About 1.7 cm. Calyx diameter: About 5 mm. Sepal length: About 1.7 cm. Sepal width, at base of "free" portion: About 3 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 144B; towards the apex, close to 143B to 143C. When opening, lower surface: Close to 137C; towards the base, close to 145A. Fully opened, upper surface: Close to 144B; towards the apex, close to 143B to 143C. Fully opened, lower surface: Close to 137A to 137B; towards the base, close to 143A to 143B.

*Peduncles*.—Length: About 2 cm. Diameter: About 1 mm. Strength: Moderately strong, Aspect: About 7.5° from the stem axis. Texture and luster: Smooth, glabrous; slightly glossy. Color: Close to 137C.

*Reproductive organs*.—Stamens: Quantity: About ten stamens per flower. Filament length: About 1.8 cm. Filament color: Close to NN155D; towards the base, fading to close to 150D. Anther length: About 2 mm. Anther shape: Oblong. Anther color: Close to 161D. Pollen: Scarce. Pollen color: Close to 155A. Pistils: Quantity: About two per flower. Pistil length: About 1.4 cm. Stigma diameter: About 4 mm. Stigma shape: Pointed, spirally curved. Stigma color: Close to NN155D. Style length: About 1 cm. Style color: Close to NN155D. Ovary color: Close to between 144A to 145C. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be suitable for USDA Hardiness Zones 5 to 9.

It is claimed:

1. A new and distinct Carnation plant named 'Hilbeagisel' as illustrated and described.

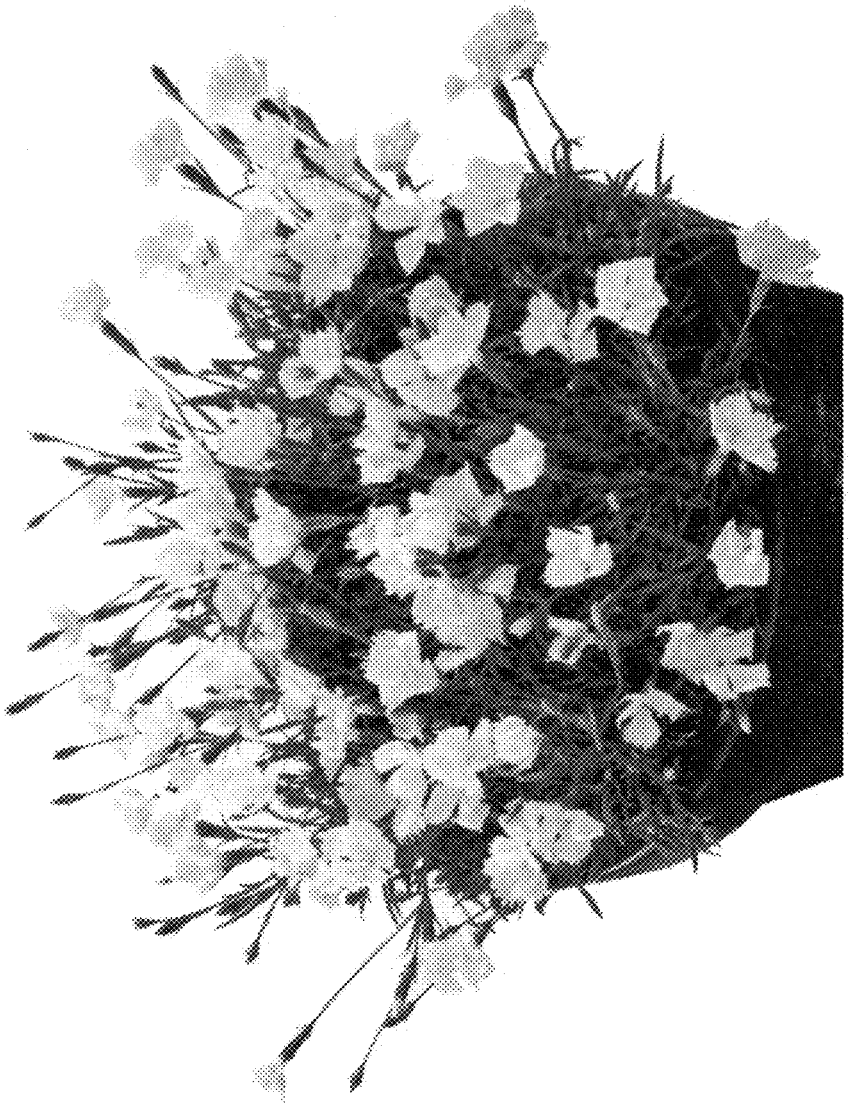

* * * * *